United States Patent [19]

Hartley et al.

[11] Patent Number: Plant 5,867

[45] Date of Patent: Jan. 27, 1987

[54] *FELICIA AMELLOIDES* HARTLEY WHITE

[76] Inventors: Richard R. Hartley; Kathleen R. Hartley, both of 5737 Busch Dr., Malibu, Calif. 90265

[21] Appl. No.: 653,958

[22] Filed: Sep. 21, 1984

[51] Int. Cl.[4] ..... A01H 5/00

[52] U.S. Cl. ..... Plt./68

[58] Field of Search ..... Plt./68

[56] References Cited

U.S. PATENT DOCUMENTS

P.P. 3,017 1/1971 Scott ..... Plt./68

P.P. 3,019 1/1971 Scott ..... Plt./68

OTHER PUBLICATIONS

*Hortus Third,* A Dictionary compiled by L. H. and E. Z. Bailey, The MacMillan Publishing Co., N.Y., pp. 472–473 (1976).

*The Standard Cyclopedia of Horticulture,* by L. H. Bailey, The MacMillan Co., N.Y., p. 1205 (1927).

*Taylor's Encyclopedia of Gardening,* (ed.) N. Taylor, Houghton Mifflin Co., Boston, p. 388, (1961).

Sunset, *New Western Garden Book,* (ed.) Sunset Magazine David E. Clark pp. 205, 297 and 298 (1979).

*Primary Examiner*—James R. Feyrer

*Attorney, Agent, or Firm*—Lyon & Lyon

[57] ABSTRACT

A new and distinct type of Felicia characterized by its vigorous growth pattern and flower color, particularly adapted for home garden use as an ornamental plant.

2 Drawing Figures

BACKGROUND

The present invention relates to a new and distinct variety of *Felicia amelloides,* the novel characteristics of which reside particularly in the color patters of the ray flowers and disk flowers, and robust growth pattern.

The new Felicia was first discovered by us in 1982. It originated from a sport branch on a blue-flowered *Felicia amelloides* in a cultivated garden in Northern California. Thereafter the new variety was successfully asexually reproduced by ourselves by rooting cuttings. This resulted in several progeny shrubs which have continually displayed the growth and flower color characteristics typical of that found on the parent sport branch.

An interesting characteristic of the new variety is the white, daisy-like flower approximately one inch in diameter. The flower is comprised of white, plate LIII on Ridgway's color plates (hereafter "R"), ray flowers when in full bloom, often dark lavender, plate XLIV, hue 61, tone b (R), at the tip or at the base of the corolla or streaked throughout the ray flower, and lemon chrome, plate IV, hue 21 (R) disk flowers at the center of the inflorescence. Another interesting characteristic is that the plant blooms abundantly and almost continuously if the dead blooms are cut or removed. Also, another interesting characteristic is that the color of the ray flowers changes with age from martius yellow, plate IV, hue 23 (R), at blooming to white, plate LIII (R) at maturity, and fading to vinaceous buff, plate XL, hue 17, tone d (R). Another characteristic of the plant is its vigorous growth and its neat appearance which makes it an excellent choice for ornamental use.

The new variety, as compared with the known variety of *Felicia amelloides,* "the blue daisy" or "blue Marguerite," is characterized by its white flower, compared to the blue flowers of the known variety.

Other distinctive characteristics of the new variety are exemplified in the accompanying illustrations.

FIG. 1 shows an adult parent shrub.

FIG. 2 is a close-up of a single adult inflorescence, illustrating the color pattern of the flowers.

TECHNICAL DESCRIPTION

The following is a description in some detail of the new variety of *Felicia amelloides, Felicia amelloides* Hartley's White.

Foliage:

*Leaves.*—Simple, opposite, exstipulate, entire, elliptic to ovate to obovate. Apex rounded, occasionally mucronate, tapering at base to a short winged petiole, to subsessile and somewhat clasping. Leaves three — nerved from based, central vein prominent, upper and lower leaf surfaces sparsely strigose, giving leaves more or less a rough texture.

*Size.*—2.5–4.5 cm long, 1.2–2.5 cm wide.

*Color.*—At maturity, foliage normal spinach green, plate V, hue 29, tone m (R), lower surfaces parrot green, plate VI, hue 31, tone k (R), new foliage slightly lighter green.

*Stem.*—Color — Newer wood light green, often with purple, strigose. Older wood becoming victoria lilac, plate 1, hue 5, tone m (R).

Flower:

*Size.*—2.7–3.5 cm diameter, 1.5–2.0 cm high, terminating in a slender, strigose, naked erect peduncle, 8–16 cm long.

*Shape.*—Solitary, involucrate, composite, radiate head. Mature heads radiate, with 11–15 ray flowers, and numerous disk flowers, Heads marcescent.

*Ray flowers.*—Pistillate, gamopetalous, ligulate with entire, strap shaped limb. Color: Martious yellow, plate IV, hue 23 (R), at blooming, maturing to white, plate LIII (R), fading to vinaceous buff, plate XI, hue 17, tone d (R). Often showing dark lavender, plate XLIV, hue 61, tone b (R) at tip and/or base of corolla or streaked throughout the ray flower.

*Disk flowers.*—Perfect, gamopetalous, regular, funnelform. Pappus forming a single series of scarious bristles to 3 mm high. Color: lemon chrome, plate IV, hue 21 (R). Styles: two-branched, yellow, exerted. Stamens: inserted, yellow. Pollen: yellow. Ovary: inferior, achenes compressed, minutely puberulent. Receptacle flat, pitted.

*Fragrance.*—slight.

Growth: Vigorous, stems adventitiously rooting at soil surface.

Season: Perennial.

Form: Evergreen subshrub, 3–6 dm upright, compact.

The above described new variety of *Felicia amelloides* displays an attractive color pattern and robust growth pattern making it an excellent ornamental shrub.

We claim:

1. A new and distinct variety of *Felicia amelloides* as described and shown herein characterized particularly by its vigorous growth pattern, and by its white ray flowers with yellow centers, as compared with the Blue Marguerite variety.

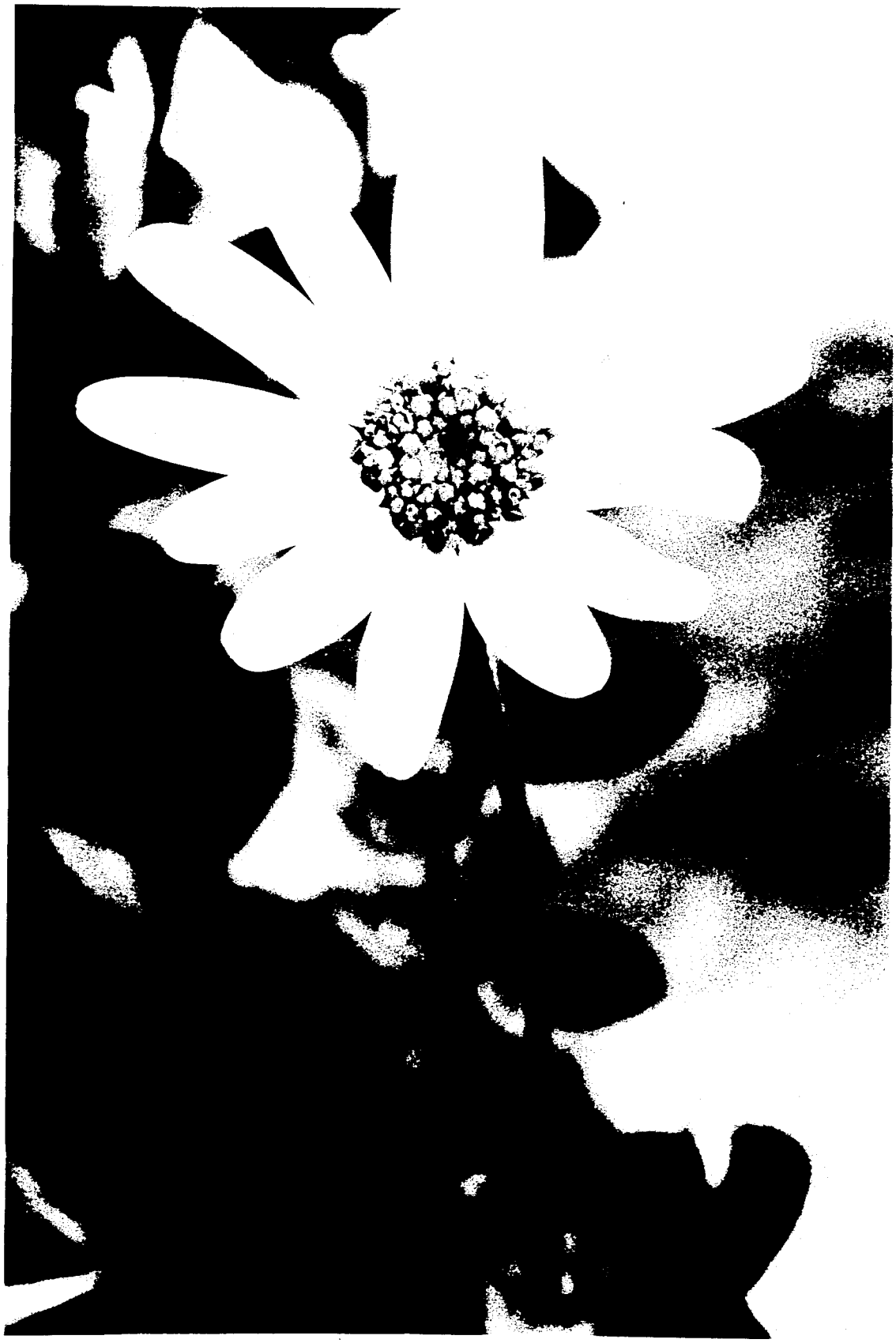

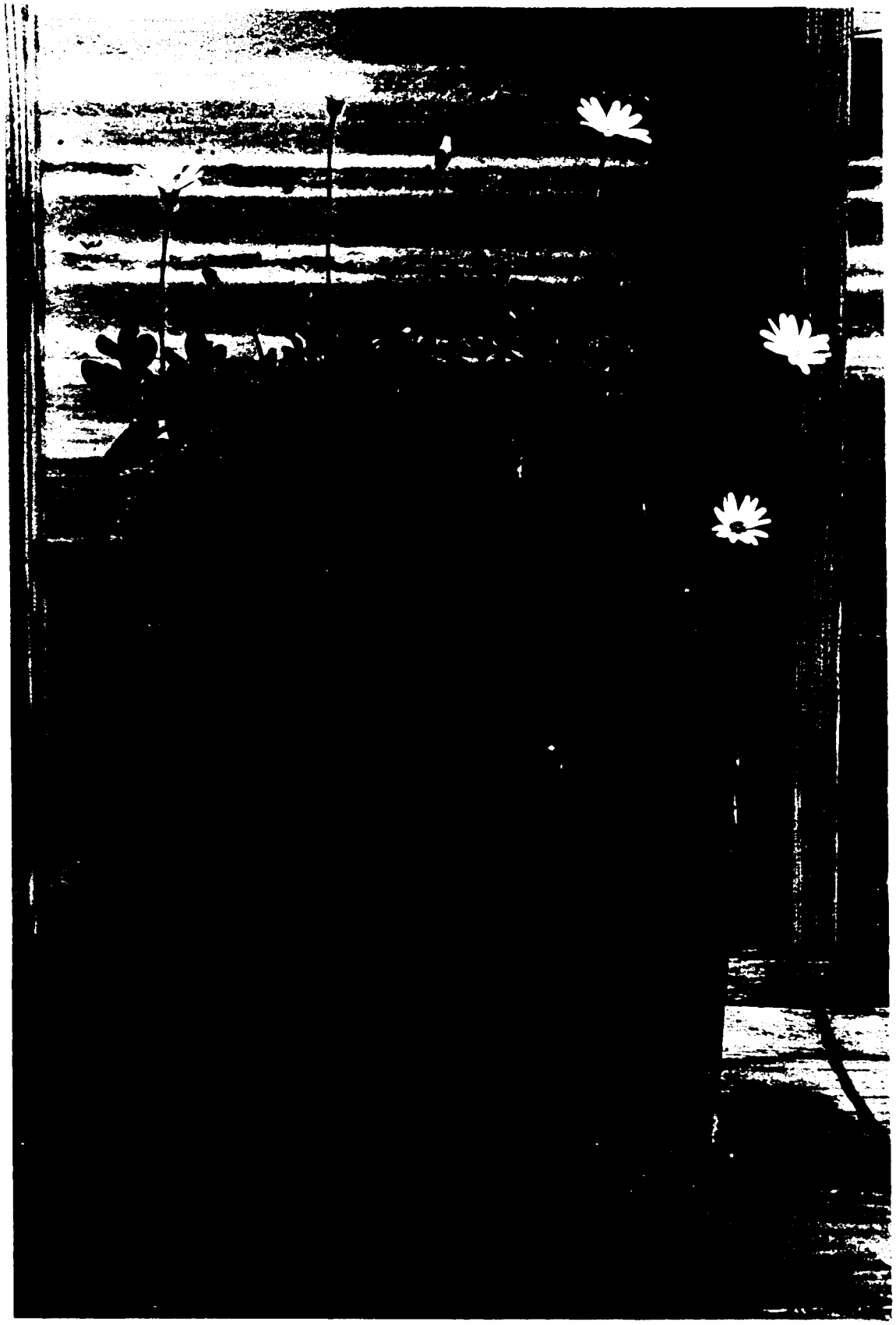

* * * * *